US00PP18001P2

(12) United States Plant Patent
Vlielander

(10) Patent No.: US PP18,001 P2
(45) Date of Patent: Sep. 11, 2007

(54) ***KALANCHOE* PLANT NAMED 'SNOWDON'**

(50) Latin Name: *Kalanchoe blossfeldiana*
Varietal Denomination: Snowdon

(75) Inventor: Ike Vlielander, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/358,921

(22) Filed: Feb. 17, 2006

(51) Int. Cl.
*A01H 5/00* (2006.01)

(52) U.S. Cl. ..... Plt./336

(58) Field of Classification Search ..... Plt./336
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Kalanchoe* plant named 'Snowdon', characterized by its large and numerous white-colored flowers; upright, uniform and vigorous growth habit; freely branching habit; dark green-colored leaves; and excellent postproduction longevity.

1 Drawing Sheet

Botanical designation: *Kalanchoe blossfeldiana.*
Cultivar denomination: 'Snowdon'.

BACKGROUND OF THE INVENTION

The present invention relates to a new and distinct cultivar of *Kalanchoe* plant, botanically known as *Kalanchoe blossfeldiana,* and hereinafter referred to by the name 'Snowdon'.

The new *Kalanchoe* is a product of a planned breeding program conducted by the Inventor in De Lier, The Netherlands. The objective of the breeding program was to create new freely-branching and freely-flowering *Kalanchoe* cultivars with attractive foliage and flower coloration.

The new *Kalanchoe* originated from a cross-pollination made by the Inventor in June, 1999 of the *Kalanchoe blossfeldiana* cultivar Simone, disclosed in U.S. Plant Pat. No. 10,238, as the female, or seed, parent with the *Kalanchoe blossfeldiana* cultivar Hillary, disclosed in U.S. Plant Pat. No. 11,798, as the male, or pollen, parent. The cultivar Snowdon was discovered and selected by the Inventor as a flowering plant within the progeny of the stated cross-pollination in a controlled environment in De Lier, The Netherlands.

Asexual reproduction of the new *Kalanchoe* by terminal vegetative cuttings in De Lier, The Netherlands, since 2001 has shown that the unique features of this new *Kalanchoe* are stable and reproduced true to type in successive generations.

BRIEF SUMMARY OF THE INVENTION

The cultivar Snowdon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Snowdon'. These characteristics in combination distinguish 'Snowdon' as a new and distinct cultivar:

1. Large and numerous white-colored flowers.
2. Upright, uniform and vigorous growth habit.
3. Freely branching habit.
4. Dark green-colored leaves.
5. Excellent postproduction longevity.

Plants of the new *Kalanchoe* can be compared to plants of the female parent, the cultivar Simone. In side-by-side comparisons conducted by the Inventor in De Lier, The Netherlands, plants of the new *Kalanchoe* differed from plants of the cultivar Simone in the following characteristics:

1. Plants of the new *Kalanchoe* were more freely branching than plants of the cultivar Simone.
2. Plants of the new *Kalanchoe* had flatter leaves than plants of the cultivar Simone.
3. Plants of the new *Kalanchoe* had better postproduction longevity than plants of the cultivar Simone.

Plants of the new *Kalanchoe* can be compared to plants of the male parent, the cultivar Hillary. In side-by-side comparisons conducted by the Inventor in De Lier, The Netherlands, plants of the new *Kalanchoe* differed from plants of the cultivar Hillary in the following characteristics:

1. Plants of the new *Kalanchoe* were more freely branching than plants of the cultivar Hillary.
2. Plants of the new *Kalanchoe* had flatter leaves than plants of the cultivar Hillary.
3. Plants of the new *Kalanchoe* had larger flowers than plants of the cultivar Hillary.
4. Plants of the new *Kalanchoe* had better postproduction longevity than plants of the cultivar Hillary.

Plants of the new *Kalanchoe* can also be compared to plants of the *Kalanchoe* cultivar White Cora, disclosed in U.S. Plant Pat. No. 13,929. In side-by-side comparisons conducted by the Inventor in De Lier, The Netherlands, plants of the new *Kalanchoe* differed from plants of the cultivar White Cora in the following characteristics:

1. Plants of the new *Kalanchoe* were larger and more vigorous than plants of the cultivar White Cora.
2. Plants of the new *Kalanchoe* had larger leaves than plants of the cultivar White Cora.

BRIEF DESCRIPTION OF THE PHOTOGRAPH

The accompanying colored photograph illustrates the overall appearance of the new *Kalanchoe,* showing the colors as true as it is reasonably possible to obtain in colored reproductions of this type. Colors in the photograph may differ slightly from the color values cited in the detailed botanical description which accurately describe the colors of the new *Kalanchoe.* The photograph comprises a side perspective view of a typical flowering plant of 'Snowdon' grown in a container.

DETAILED BOTANICAL DESCRIPTION

In the following description, color references are made of The Royal Horticultural Society Colour Chart, 1995 Edition, except where general terms of ordinary dictionary significance are used. Plants used for the aforementioned photograph and for the description were grown during the autumn in De Lier, The Netherlands, in a glass-covered greenhouse. During the production of the plants, day temperatures ranged from 18° C. to 20° C.; night temperatures averaged 18° C.; and light levels ranged from 10,000 to 55,000 lux. Unrooted cuttings were directly stuck in 12.5-cm containers and received long day/short night conditions (more than 14 hours of light) for about three weeks; plants then received photoinductive short day/long night conditions (minimum 14 hours darkness) until flowering. Plants were about 14 weeks old from an unrooted cutting when the photograph and the description were taken.

Botanical classification: *Kalanchoe blossfeldiana* cultivar Snowdon.

Parentage:

*Female or seed parent.*—*Kalanchoe blossfeldiana* cultivar Simone, disclosed in U.S. Plant Pat. No. 10,238.

*Male, or pollen, parent.*—*Kalanchoe blossfeldiana* cultivar Hillary, disclosed in U.S. Plant Pat. No. 11,798.

Propagation:

*Type cutting.*—Terminal vegetative cuttings.

*Time to initiate roots, summer.*—About 14 days at 21° C.

*Time to initiate roots, winter.*—About 16 days at 21° C.

*Time to produce a rooted cutting, summer.*—About 15 days at 21° C.

*Time to produce a rooted cutting, winter.*—About 18 days at 21° C.

*Root description.*—Fine, fibrous; grayish white in color.

*Rooting habit.*—Freely branching; dense.

Plant description:

*Form.*—Upright, uniform and vigorous growth habit. Very freely flowering with numerous compound cymes. Inverted triangle with rounded crown. Appropriate for 10 to 15-cm containers.

*Crop time.*—About 13 to 16 weeks; 3 to 4 weeks under long day/short night conditions followed by 10 to 12 weeks of short day/long night conditions.

*Plant height at flowering.*—About 18 cm.

*Plant diameter at flowering.*—About 21 cm.

*Branching habit.*—Freely branching; typically eight to ten lateral branches develop per plant. Pinching (removal of terminal apex) is not required but will enhance lateral branch development.

*Lateral branch description.*—Length: About 10 cm to 14 cm. Diameter: About 2 mm to 5 mm. Internode length: About 2 cm to 3 cm. Aspect: Erect. Strength: Moderately strong. Texture: Smooth, glabrous. Color: 138A.

*Foliage description.*—Arrangement: Opposite, simple; generally symmetrical. Quantity per plant: About 8 to 13 mature leaves and 14 to 22 generative leaves. Length: About 12 cm. Width: About 9 cm. Shape: Ovate to elliptic. Apex: Obtuse. Base: Acute. Margin: Crenate. Texture: Leathery, glabrous and succulent. Color: Developing and fully expanded leaves, upper surface: 135A; venation, 135A. Developing and fully expanded leaves, lower surface: 137A; venation, 137A. Petiole length: About 1.5 cm. Petiole diameter: About 4 mm to 7 mm. Petiole texture, upper and lower surfaces: Smooth, glabrous. Petiole color, upper and lower surfaces: 135A.

Flower description:

*Flower type and habit.*—Single flowers arranged in compound dichasial cymes that arise from leaf axials. Freely flowering; more then 25 open flowers pet lateral branch and more than 150 open flowers per plant. Flowering continuously for at least eight weeks. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about ten to twelve weeks are required. Actual time to flower is primarily dependent upon temperature and light intensity.

*Post-production longevity.*—Excellent post-production longevity; plants maintain good foliage and flower substance for about 70 days under interior environmental conditions. Individual flowers last about 25 days on the plant.

*Flower diameter.*—About 1.8 cm.

*Flower height.*—About 1.5 cm.

*Flower buds.*—Shape: Initially oblong, becoming tubular ovoid with development. Length: About 1.5 cm. Width: About 2 mm. Color: 4C to 4D.

*Petals.*—Quantity: Four fused at base. Length: About 8 mm. Width: About 7 mm. Aspect: Flat to slightly upright. Shape: Ovate. Apex: Obtuse to acute. Margin: Entire. Texture: Glabrous, smooth. Color: When opening, upper surface: 4B. When opening, lower surface: 4C. Fully opened, upper and lower surfaces: 155D.

*Sepals.*—Quantity: Four fused at base. Length: About 8 mm. Width: About 2 mm. Aspect: Erect. Shape: Oblong. Apex: Acute. Base: Obtuse. Margin: Entire. Texture: Glabrous, smooth. Color, immature, upper and lower surfaces: 141D. Color, mature, upper and lower surfaces: 141C.

*Peduncles.*—Length: About 4 mm to 7 mm. Diameter: About 1 mm. Aspect: Erect. Strength: Strong, flexible. Texture: Smooth, glabrous. Color: 141A.

*Reproductive organs.*—Stamens: Quantity per flower: Eight. Anther shape: Elliptic; flat. Anther size: About 0.3 mm. Anther color: Close to 150D. Pollen amount: Scarce. Pollen color: Close to 12A. Pistils: Quantity per flower: Four. Style length: About 1 mm. Style color: 138D. Stigma shape: Flat, rounded. Stigma color: 8D. Ovary color: 138D.

*Seed.*—Length: About 0.1 mm. Diameter: About 0.05 mm. Color: Close to 166C.

Disease/pest resistance: Plants of the new *Kalanchoe* have not been observed to be resistant to pathogens and pests common to *Kalanchoes.*

Temperature tolerance: Plants of the new *Kalanchoe* have been observed to tolerate low temperatures of 16° C. and high temperatures of 35° C.

Garden performance: Plants of the new *Kalanchoe* perform have been observed to perform well in the garden and are tolerant to rain and wind.

It is claimed:

1. A new and distinct cultivar of *Kalanchoe* plant named 'Snowdon', as illustrated and described.

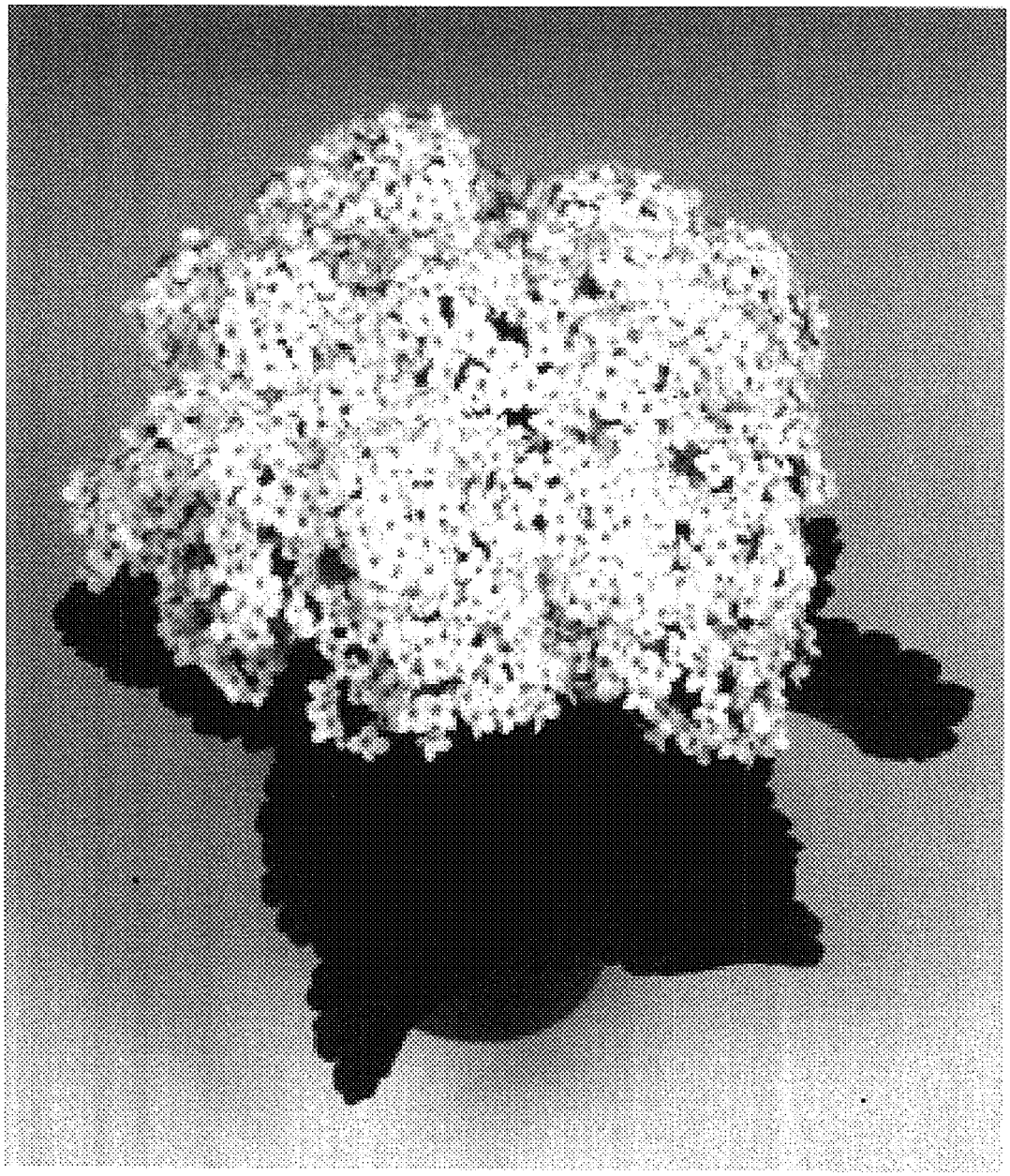

* * * * *